US006685812B2

(12) United States Patent
Miles

(10) Patent No.: US 6,685,812 B2
(45) Date of Patent: Feb. 3, 2004

(54) MOVEMENT OF PARTICLES USING SEQUENTIALLY ACTIVATED DIELECTROPHORETIC PARTICLE TRAPPING

(75) Inventor: Robin R. Miles, Danville, CA (US)

(73) Assignee: The Regents of the University of California, Oakland, CA (US)

( * ) Notice: Subject to any disclaimer, the term of this patent is extended or adjusted under 35 U.S.C. 154(b) by 390 days.

(21) Appl. No.: 09/757,248

(22) Filed: Jan. 9, 2001

(65) Prior Publication Data

US 2002/0088712 A1 Jul. 11, 2002

(51) Int. Cl.[7] .................... G01N 27/447; G01N 27/453; G01N 1/00; C12Q 1/68; C12P 19/34

(52) U.S. Cl. ....................... 204/547; 204/643; 436/174; 435/6; 435/287.2; 435/91.2

(58) Field of Search ................................ 204/450, 451, 204/547, 600, 643; 435/6, 287.2, 91.2; 436/174

(56) References Cited

U.S. PATENT DOCUMENTS 5,454,472 A * 10/1995 Benecke et al. ......... 209/127.1
6,149,789 A * 11/2000 Benecke et al. ............ 204/547
6,319,472 B1 * 11/2001 Ackley et al. ............ 422/68.1

FOREIGN PATENT DOCUMENTS

WO 9734689 A1 * 9/1997

* cited by examiner

*Primary Examiner*—Nam Nguyen
*Assistant Examiner*—Alex Noguerola
(74) *Attorney, Agent, or Firm*—Eddie E. Scott; L. E. Carnahan; Alan H. Thompson

(57) ABSTRACT

Manipulation of DNA and cells/spores using dielectrophoretic (DEP) forces to perform sample preparation protocols for polymerized chain reaction (PCR) based assays for various applications. This is accomplished by movement of particles using sequentially activated dielectrophoretic particle trapping. DEP forces induce a dipole in particles, and these particles can be trapped in non-uniform fields. The particles can be trapped in the high field strength region of one set of electrodes. By switching off this field and switching on an adjacent electrodes, particles can be moved down a channel with little or no flow.

16 Claims, 3 Drawing Sheets

MOVEMENT OF PARTICLES USING SEQUENTIALLY ACTIVATED DIELECTROPHORETIC PARTICLE TRAPPING

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention is directed to PCR sample preparation, particularly to the manipulation of particle in a sample fluid using dielectrophoretic forces to concentrate and move samples in an electrophoretic channel, and more particularly to movement of particles by sequentially activated/deactivated electrodes position along a length of a channel.

Extensive efforts are being carried out to enable sample preparation for various amplication, such as to provide PCR sample preparation for counter biological warfare applications, as well as for a clinical tool to determine genetic information. A key element of the sample preparation process is to enable controlled concentration and/or movement of DNA, for example, prior to detection.

The present invention enables manipulation of DNA and cells/spores using dielectrophoretic (DEP) forces to perform sample preparation protocols for polymerized chain reaction (PCR) based assays. The invention utilizes a series of electrodes located along a length of an electrophoretic channel. Since DEP forces induce a dipole in the sample particles, these particles can be trapped in non-uniform fields produced by electrodes located along a length of the channel. By switching on and off sequentially located electrodes, the electric field s produced thereby cause the particles to be moved down a channel and/or concentrated in the channel, with little or no flow. Thus, the invention provides movement of particles using sequentially activated dielectrophoretic particle trapping.

SUMMARY OF THE INVENTION

It is an object of the present invention to provide movement and concentration of particles in an electrophoretic channel.

A further object of the invention is to provide movement of particles using sequentially activated dielectrophoretic particle trapping.

A further object of the invention is to enable manipulation of DNA and cells/spores using dielectrophoretic forces to perform sample preparation protocols for PCR based assays.

Another object of the invention is to provide an electrophoretic channel with sets of electrodes, which can be sequentially activated to cause movement of particles down the channel.

Another object of the invention is to photolithographically pattern electrodes along a length of dielectrophoretic channel, whereby controlled activation/deactivation of the various electrodes enable concentration of or movement of the particles with little or no sample fluid flow.

Another object of the invention is to provide an electrophoretic channel with sets of electrodes located along a length or the channel whereby particles can be trapped in the high electric field strength produced by the electrodes, and sequential activation/deactivation of those electric field cause movement of the particles down the channel.

Other objects and advantages of the present invention will become apparent from the following description and accompanying drawings. Basically the present invention provides for movement of particles using dielectrophoretic (DEP) forces. The particles are moved using sequentially activated dielectrophoretic particle trapping. The sequential particle trapping is carried out by sets of electrodes located along a length of an electrophoretic channel, and subsequent adjacent electrodes are activated to cause the movement of the particles down the channel. The electrodes may be photolithographically patterned on the bottom and the top of the flow channel, with a number of electrode segments on either the top or bottom with a single electrode on the respective bottom or top of the channel. An alternating current (AC) signal is placed between an electrode segment and the opposite electrode to produce an electric field which traps the charged particles due to the dielectrophoretic forces imposed thereon. Switching of the AC signal from an electrode segment to a downstream electrode segment results the particles being drawn downstream by the changing electric fields. By control of the AC signal on the electrodes, the particles can be collected at any desired point in the channel or movement along the channel as need for PCR assays, for example.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

Figure 1:
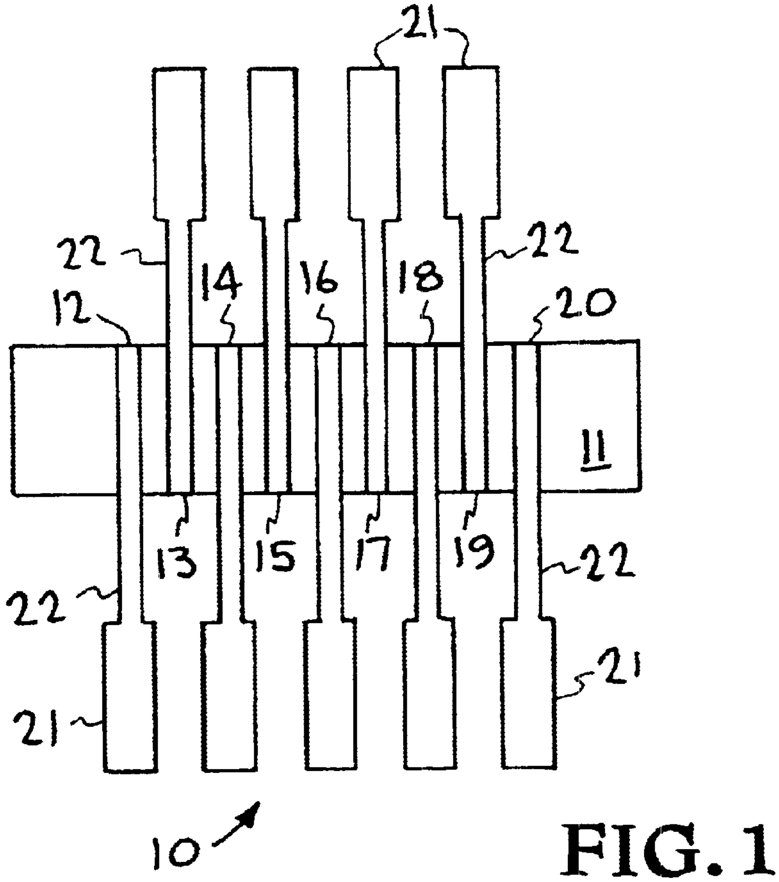
FIG. 1 is a top view of an embodiment of a patterned set of electrodes or electrode segments located on a top surface of a fluidic channel.

The present invention is directed to the manipulation of DNA and cells/spores using dielectrophoretic (DEP) forces to perform sample preparation protocols for polymerized chain reaction (PCR) based assays. More specifically, the invention is directed to movement of particles using sequentially activated DEP particle trapping. The invention enables the movement of materials along a fluidic channel with little or no flow. DEP forces induce a dipole in the particles (a negative charge for example) and these charged particles can be trapped in non-uniform electric fields. The particles are trapped in high electric field strength regions of a first set of several sets of electrodes located along the fluidic channel, and by switching off the electric field in the first set of electrodes and switching on the adjacent downstream set of electrodes, particles can be moved down the fluidic channel. The set of electrodes may comprise a number of smaller electrodes, such as fingers or segments of interdigitated electrodes on the top of the fluidic channel and a long or larger single electrode at the bottom of the channel, or vice versa, and the electric fields are generated between any of the small electrodes or electrode segments and single electrode. Thus, as seen in the drawings and described in detail hereinafter, as the electric field is changed from one small electrode to the next small electrode the particles are drawn down the fluidic channel so as to enable control, concentration, and appropriate movement of the particles for assay purposes.

A set of small electrodes may be photo-lithographically patterned on the top as shown in FIG. 1, or on the bottom, of a fluidic or flow channel. A single electrode (larger) is patterned on the bottom, as shown in FIG. 1, or on the top of the flow channel. An alternating current (AC) source is connected between the sets of small electrodes and the single electrode such that an AC signal can be placed between any one of the small electrodes on the top of the channel and the single electrode on the bottom, as shown, thereby producing an electric field therebetween. The particles are attracted to the high electric field gradient at the smaller electrode. When it is desired to move a particle along the channel the small electrode will be switched off and the next (downstream) small electrode will be switched on (activated), causing the particle to move to and trapped in the electric field of that next electrode. Thus, the particles can be "walked" down the channel under full control of particle movement, with little or no flow through the channel.

Figure 2:
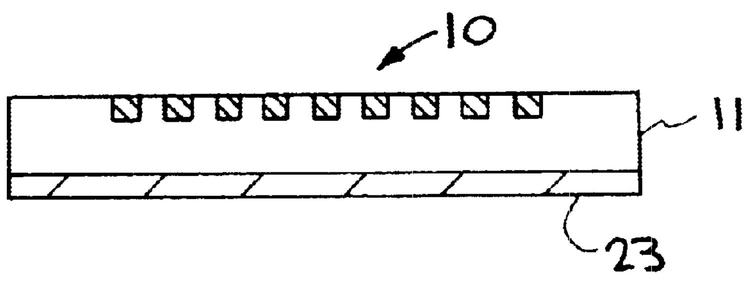
FIG. 2 is a side view of the fluid channel and electrode of FIG. 1 shown a single electrode on the bottom surface of the fluidic channel.
Figure 3:
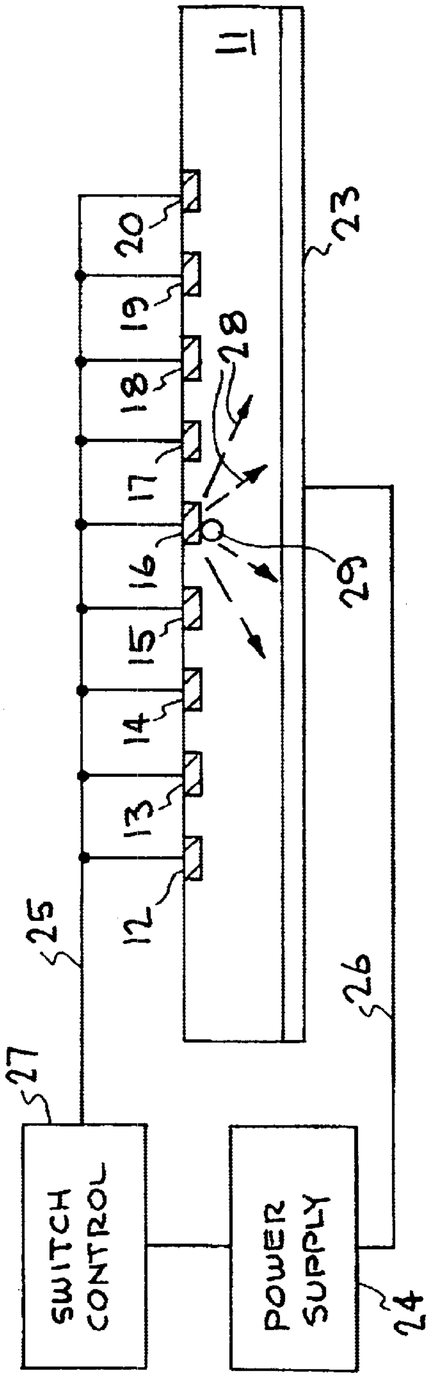
FIG. 3 illustrates electric fields formed between the electrodes of FIG. 2 when an AC signal is directed across the electrodes, causing particle retainment or concentration.
Figure 4:
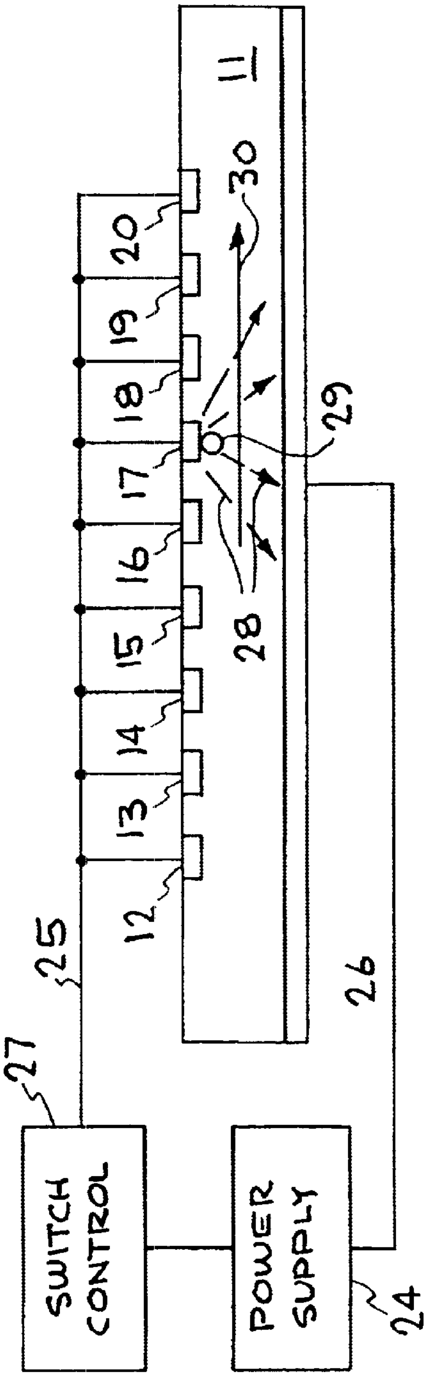
FIG. 4 illustrates the movement of particles along the fluidic channel when the AC signal is directed to subsequent downstream electrodes or electrode segments.

An embodiment of an electrode configuration is illustrated in FIGS. 1 and 2, with FIGS. 3 and 4 illustrating the electric field change causing movement of the particles through the fluidic or flow channel. FIG. 1 is a top view of an electrode configuration located in the top or upper surface of a channel, while FIG. 2 is a side view of the electrode configuration of Figure.

As shown in FIGS. 1 and 2, a set of small electrodes or electrode segments, generally indicated at 10 are patterned on a flow channel 11, with the electrodes 12, 13, 14, 15, 16, 17, 18, 19, and 20 located in the channel 11 and each connected to an electrical contact pad 21 via leads 22 as known in the photolithographic art. A single electrode 23 is patterned along a length of channel 11, as seen in FIG. 2 on a bottom surface of the channel. As pointed out above, the small electrode 12–20 can be located on the bottom of the channel 11 and the single electrode 23 location on the top of the channel 11.

As shown in FIGS. 3 and 14, the electrodes 12–20 and 23 of FIG. 1 are selectively connected to an AC power source 24 via leads 25 and 26, with a switch control mechanism 27 mounted in lead 25, to selectively connect the AC signal to any one of the electrodes 12–20, such signal switching mechanisms being known in the art. As shown in FIG. 3, an electrical signal (charge) is placed across electrode 16 and electrode 23 producing electric field lines 28, whereby a particle 29 is attached to electrode 16. As the next (adjacent) downstream electrode 17 is switched on and electrode 16 is switched off the electric field is generated between electrodes 17 and 23 causing the particle 29 to attach to electrode 17, as seen in FIG. 4, whereby sequential activation of downstream electrodes 18, 19, and 20 cause the particle to move downstream as indicated by arrow 30. Thus movement of particles through the flow channel 11 is effectively controlled by electrodes 10 and 23, via sequential activation of electrodes 12–20.

Figure 5:
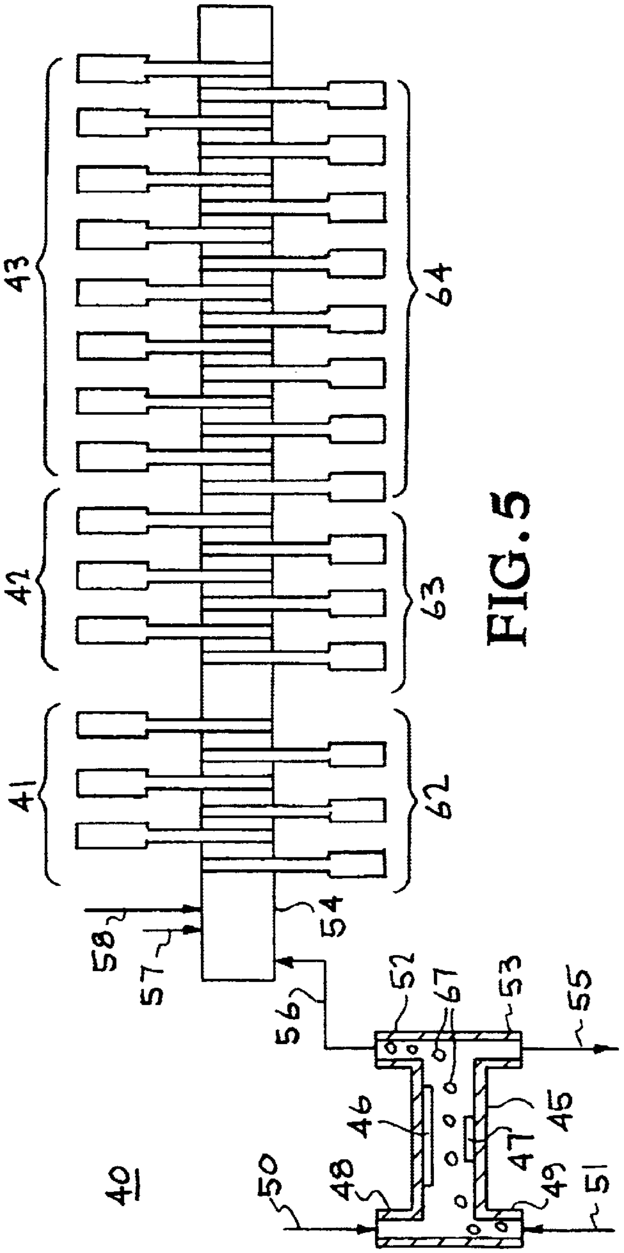
FIG. 5 is a top diagramatic view of an embodiment of a sample preparation/assay system utilizing the sequentially activated electrode arrangement illustrated in FIGS. 1–4.
Figure 6:
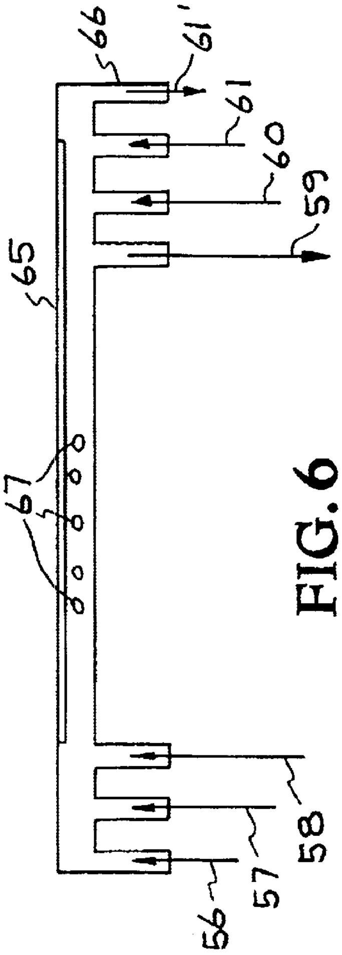
FIG. 6 is a side view of a portion of the FIG. 5 system.

FIGS. 5 and 6 schematically illustrate a PCR sample preparation system which incorporates sequentially activated electrodes, as exemplified above relative to FIGS. 1–4, with FIG. 5 being a top view of the overall system and FIG. 6 being a side view of a portion of the FIG. 5 system. As shown the system incorporates four (4) sections or functions which include sample fractionation indicated at 40, sample concentration indicated at 41, DNA concentration indicated at 42, and DNA motion/reagent mix indicated at 43. The sample fractionation section 40 includes a flow channel 45 in which electrodes 46–47 for DEP are mounted, with channel 45 having inputs or inlets 48 and 49 into which are directed a focusing buffer 50 and a sample 51 (from an aerosol collector, for example, and outlets 52 and 53, connected to a channel 54 to waste 55.

Channel 54 extends through sections 41–43 of the system and includes 3 inlets, a sample inlet 56, a lysing solution inlet 57, and a focusing buffer inlet 58, see FIG. 6, and is provide with a waste outlet 59, a PCR reagent inlet 60 and outlet 61, and an exit 61'. The channel 54 is also provided with electrode sets indicated at 62 for section 41, 63 for section 42 and 64 for section 43 and with a single electrode 65, see FIG. 6, which extends the length of electrode sets 62, 63 and 64. As in FIGS. 1–4, the electrode sets 62–64 and single electrode 65 are electrically connected to an AC power source via a switching mechanism, as in FIGS. 3–4. The channel 54 terminals via a detector which includes a potentiometer 66. As charged particles 67 from outlet 52 of channel 45 of sample fractionation section 40 pass along channel 54 the electrodes of electrode sets 62, 63 and 65, as each sequentially activated to control the concentration of the particles via electrical fields produced by the sequentially activated electrodes. As seen in FIGS. 5 and 6 a sample 56 containing particles 67 is introduced into flow channel 54, wherein the particles (cells and spores) are captured on the electrodes of electrode set 62 by DEP forces. A focusing buffer 51 and a lysing solution 57 are introduced into channel 54, the lysing solution 57 breaking open the spores to release the DNA. The DNA travels downstream to another set 63 of electrodes where the DNA is captured. The DNA is walked down the channel 54 to a low-flow area, section 43, via electrode set 64, where PCR reagents 60 are introduced. The sample is then released for the PCR process and detection.

It has thus been shown that the present invention enables movement and concentration of particles in a fluidic channel via DEP forces through sequentially activated electrodes which produce particle trapping via electric fields. By changing the electric field within the channel the particles can be moved along the channel with little or no flow. The invention is particularly applicable for use in counter biological warfare as well as a clinical tool to determine genetic information via PCR processing.

While particular embodiments of the invention have been described and illustrated to exemplify and teach the principles of the invention, such are not intended to be limiting. Modifications and changes may become apparent to those skilled in the art and it is intended that the invention be limited only by to scope of the appended claims.

What is claimed is:

1. In a sample preparation system using a fluidic channel and dielectrophoretic forces, the improvement comprising:

providing a plurality of electrodes along the fluidic channel which comprises at least one electrode configuration having a single electrode on one surface of the fluidic channel and a series of electrodes on another surface of the fluidic channel, and controlling movement of sample particles along the fluidic channel by the electrode configuration to carry out sequentially activated dielectrophoretic particle trapping.

2. The improvement of claim 1, wherein the movement of sample particles by particle trapping is carried out by the at least one electrode configuration producing sequential electric fields along a length of the fluidic channel.

3. The improvement of claim 2, wherein the sequential electric fields are produced by the plurality of electrodes operatively connected to an AC power supply via a switching mechanism.

4. The improvement of claim 3, wherein said AC power supply is connected to said single electrode and sequentially connected to each electrode of said series of electrodes, whereby a series of electric fields are created along a length of the fluidic channel.

5. The improvement of claim 4, wherein said single electrode is located at the bottom of the fluidic channel and the series of electrodes are located at the top of the fluidic channel, or vice versa.

6. The improvement of claim 4, wherein said fluid channel is provided with a plurality of said electrode configurations in spaced relation along a length of said fluidic channel.

7. A method for manipulation of DNA and cells/spores using dielectrophoretic forces to perform sample preparation protocols for PCR based assays, comprising:

providing a flow channel, and controlling the movement of sample particles through the flow channel using sequentially activated dielectrophoretic particle trapping is carried out by a series of electrodes defining a single electrode on one surface of the flow channel, and a plurality of electrodes on an opposite surface of the flow channel.

8. The method of claim 7, wherein the sequentially activated dielectrophoretic particle trapping is carried out by forming sequential electric fields by said series of electrodes along a length of the flow channel such that the sample particles are moved from one electric field to an adjacent downstream electric field.

9. The method of claim 8, wherein forming of the sequential electric fields is carried out by sequentially activating and deactivating said series of electrodes positioned along a length of the flow channel.

10. The method of claim 9, additionally including forming the series of electrodes by photolithographically patterning the electrodes on the top and bottom of the flow channel.

11. The method of claim 9, wherein a power supply is electrically connected to the single electrode and sequentially connected to the plurality of electrodes for producing sequential electric fields therebetween, whereby a sample particle is moved along a length of the flow channel by the sequential electric fields.

12. The method of claim 11, additionally including forming a plurality of spaced electrode configurations along a length of the flow channel, each electrode configuration having a single electrode on one surface of the flow channel and a plurality of electrodes on an opposite surface of the flow channel, and providing means to direct an electric signal to the single electrode and to selectively direct an electric signal to one or more of the plurality of electrodes for generating or removing electric fields along a length of the flow channel.

13. In a system for PCR sample preparation comprising a fluid channel through which samples are directed, the improvement comprising means for controlling movement of the samples through the fluid channel using sequentially activated dielectrophoretic particle trapping, said means includes a plurality of patterned electrodes on a surface of the fluid channel and a single electrode one an opposite surface of the fluid channel, and a power supply connected to said single electrode and sequentially connected to said plurality of patterned electrodes.

14. The improvement of claim 13, wherein said means additionally includes a mechanism for sequentially connecting said power supply to said plurality of electrodes, whereby deactivation of one electrode and activation of an adjacent electrode produces a sequence of electric fields along the fluid channel causing controlled movement of trapped samples along the fluid channel.

15. The improvement of claim 14, wherein said power supply comprises an AC power source.

16. In a system for PCR sample preparation comprising a fluid channel through which samples are directed, the improvement comprising means for controlling movement of the samples through the fluid channel using sequentially activated dielectrophoretic particle trapping, said means including a plurality of electrode configurations spaced along a length of the fluid channel, each electrode configuration including a plurality of electrodes on a surface of the fluid channel and a single electrode on an opposite surface of the fluid channel, each electrode configuration being operatively connected to a power supply to produce selective electric fields between electrodes of each said electrode configuration, for trapping, moving, and/or concentrating samples in the fluid channel.

* * * * *